(12) United States Patent
Rogers et al.

(10) Patent No.: US 10,545,152 B2
(45) Date of Patent: Jan. 28, 2020

(54) METHOD AND COMPOSITION USING A QUATERNARY AMMONIUM COMPOUND

(71) Applicant: ARCIS BIOTECHNOLOGY HOLDINGS LIMITED, Warrington (GB)

(72) Inventors: Jan Rogers, Chester (GB); Paul Reeves, Liverpool (GB); Carlos Toro Rueda, Madrid (ES)

(73) Assignee: ARCIS BIOTECHNOLOGY HOLDINGS LIMITED, Warrington (GB)

( * ) Notice: Subject to any disclaimer, the term of this patent is extended or adjusted under 35 U.S.C. 154(b) by 0 days.

(21) Appl. No.: 15/748,904

(22) PCT Filed: Jul. 28, 2016

(86) PCT No.: PCT/GB2016/052316
§ 371 (c)(1),
(2) Date: Jan. 30, 2018

(87) PCT Pub. No.: WO2017/017457
PCT Pub. Date: Feb. 2, 2017

(65) Prior Publication Data
US 2018/0267048 A1 Sep. 20, 2018

(30) Foreign Application Priority Data

Jul. 30, 2015 (GB) .................................. 1513492.7
Jan. 22, 2016 (GB) .................................. 1601185.0

(51) Int. Cl.
| | |
|---|---|
| *C12Q 1/68* | (2018.01) |
| *G01N 33/58* | (2006.01) |
| *C12Q 1/6806* | (2018.01) |
| *C12Q 1/6816* | (2018.01) |
| *C12Q 1/686* | (2018.01) |

(52) U.S. Cl.
CPC ......... *G01N 33/582* (2013.01); *C12Q 1/6806* (2013.01); *C12Q 1/6816* (2013.01); *C12Q 1/686* (2013.01); *C12Q 2521/107* (2013.01); *C12Q 2527/125* (2013.01)

(58) Field of Classification Search
None
See application file for complete search history.

(56) References Cited

U.S. PATENT DOCUMENTS

| | | | |
|---|---|---|---|
| 5,728,822 A | 3/1998 | Macfarlane | |
| 7,456,281 B2 | 11/2008 | Dujols | |
| 2003/0087279 A1* | 5/2003 | Shao | ............... C12Q 1/6809 435/6.11 |
| 2012/0322058 A1 | 12/2012 | Regan et al. | |

FOREIGN PATENT DOCUMENTS

| | | |
|---|---|---|
| CN | 103290107 A | 9/2013 |
| JP | 2005192554 | 7/2005 |
| WO | 02090539 A2 | 11/2002 |
| WO | 2013175188 A1 | 11/2013 |
| WO | 2014155078 A1 | 10/2014 |
| WO | 2016051177 A2 | 4/2016 |

OTHER PUBLICATIONS

William C. Griffin, "Calculation of HLB Values of Non-Ionic Surfactants," Atlas Power Company, Wilmington, Del., Journal of the Society of Cosmetic Chemists, Supplied by the British Library, Nov. 13, 2018, 8 pages.
Zhou et al., "Closed-Tube Genotyping with Unlabeled Oligonucleotide Probes and a Saturating DNA Dye", Clinical Chemistry 50:8, 2004, 8 pages, pp. 1328-1335.
International Search Report for PCT Application No. PCT/GB2016/052316 dated Oct. 17, 2016, 5 pages.
GB Search Report for GB Application No. GB1601185.0 dated Oct. 21, 2016, 4 pages.
International Preliminary Report on Patentability for corresponding International Application No. PCT/GB2016/052316 dated Jan. 30, 2018, 8 pages.
"Hydrophilic-lipophilic balance," from Wikipedia (https://en.wikipedia.org/wiki/Hydrophilic-lipophilic_balance) May 9, 2016, 2 pages.

* cited by examiner

*Primary Examiner* — James Martinell
(74) *Attorney, Agent, or Firm* — Hoffman Warnick LLC

(57) ABSTRACT

A method (e.g. high resolution melting analysis) of determining of the presence or absence of a target nucleic acid in a sample, e.g. a biological sample, the method comprising steps of:•(a) contacting the sample with a composition comprising•(i) a quaternary ammonium compound, e.g. 3-(trimethoxysilyl) propyl-dimethyl octadecyl ammonium chloride (3-TPAC) or a precursor thereof, in order to release the nucleic acids from said sample; and•(b) contacting the sample with a probe which is capable of interacting with the nucleic acid sequence; and•(c) observing and/or measuring a property of the sample, e.g. fluorescence from a dsDNA binding dye.

7 Claims, 2 Drawing Sheets

METHOD AND COMPOSITION USING A QUATERNARY AMMONIUM COMPOUND

The present invention relates to a method of direct detection of nucleic acids (DNA and/or RNA) in a sample. In particular the invention relates to a method which does not involve amplification or further upstream processing.

Methods of target nucleic acid detection are well known in the art and have several applications across diagnostics, pharmaceuticals, and research. For example, such methods are used for the diagnosis of many medical conditions, in the manufacture of a number of pharmaceuticals, and in genetic fingerprinting and crime scene investigations. The present invention can find utility across these areas. The present invention has particular utility in, for example, diagnostics and personalised medicine.

However current methods of determining the presence or absence of a specific DNA or RNA sequence in a sample involve a series of steps including tedious purification steps and often requires on site specialist equipment.

Genetic material, in particular RNA, is very fragile and often degrades very quickly. In particular it is difficult to store and transport RNA. Currently RNA must be purified prior to storage or transport. Furthermore RNA must be purified prior to its use in an amplification process such as a reverse transcription polymerase chain reaction (RT-PCR) where, typically, complementary DNA (cDNA) is produced from the RNA and a target sequence from the cDNA is subsequently amplified. Typically once RNA has been purified it is stored in nuclease-free water at −80° C. or at −20° C. following ethanol precipitation. However storage at such low temperatures is often not possible and is inconvenient and costly. Storage under such conditions is frequently difficult when samples are taken in less developed countries such as Africa where diseases such as malaria are prevalent. Furthermore ethanol precipitation has the disadvantage that samples must be pelleted and dissolved in buffer each time a sample is required.

Techniques are known by which the presence or absence of a target DNA and/or RNA component may be performed in situ i.e. within the cell. However the fragile nature of RNA in particular limits these methods. Furthermore the nature of the probe is limited as it must be able to penetrate the cell wall. Such methods are also expensive and complex.

It is an aim of the present invention to provide improved means for identifying target nucleic acid sequences in a sample.

According to a first aspect of the present invention there is provided a method of determining of the presence or absence of a target nucleic acid component in a sample, the method comprising steps of:
  (a) contacting the sample with a composition comprising
     (i) a quaternary ammonium compound or a precursor thereof; and
  (b) contacting the sample with a probe which is capable of interacting with the nucleic acid sequence; and
  (c) observing and/or measuring a property of the sample.

The sample used in the method of the present invention may be taken from a plant or from an animal, for example a human.

In some embodiments the sample is obtained from a plant. In such embodiments the method may be used to detect whether the plant is infected with a disease or if the plant has a genetic defect.

The sample used in the method of the present invention is preferably a sample of bodily fluid or tissue obtained from a human or other animal. Preferably the sample is a sample of bodily fluid or tissue obtained from a human. Suitable bodily fluids include blood and blood components, mucus, saliva, urine, vomit, faeces, sweat, semen, vaginal secretion, tears, pus, sputum and pleural fluid. Suitable tissues include cancer cells, connective tissue cells, epithelial cells, nervous tissue cells, muscle tissue cells and endodermal, mesodermal or ectodermal cells.

It is particularly advantageous that bodily fluid or tissue samples can be used directly in the method of the present invention. For example it is possible to carry out the method of the present invention on a whole blood sample or a sputum sample.

In some preferred embodiments the sample is a blood sample, for example a whole blood sample.

In some preferred embodiments, the sample is a tissue sample, for example cancer cells.

When the sample is obtained from a plant it may comprise a portion of the leaves, roots, stem, sap, flower, seed or fruit or the plant.

The method of the present invention may be used to determine the presence or absence of any suitable type of nucleic acid. It may be used to determine the presence or absence of DNA and/or RNA.

Suitable types of DNA include genomic DNA from a human, animal or microorganism, transcriptomic DNA from a human or animal, plasmid DNA, DNA aptamers and cosmid DNA.

Suitable types of RNA include messenger RNA (mRNA), ribosomal RNA (rRNA), signal recognition particle RNA (SRP RNA), transfer RNA (tRNA), transfer messenger RNA (tmRNA), small nuclear RNA (snRNA), small nucleolar RNA (snoRNA), SmY RNA, small Cajal body specific RNA (scaRNA), guide RNA (gRNA), ribonuclease P (RNase P), ribonuclease MRP (RNase MRP), Y RNA, telomerase RNA component (TERC), spliced leader RNA (SL RNA), antisense RNA (asRNA), cis-natural antisense RNA (cis-NAT), long noncoding RNA (lncRNA), microRNA (miRNA), piwi-interacting RNA (piRNA), small interfering RNA (siRNA), trans-acting siRNA (tasiRNA), repeat associated siRNA (rasiRNA), 7SK RNA (7SK), viral RNA and RNA aptamers. Suitably these types of RNA may be from, for example, a human, animal, or microorganism.

DNA and/or RNA from microorganisms may be from bacteria, fungi or viruses.

Step (a) of the method of the present invention involves contacting the sample with a composition comprising (i) a quaternary ammonium compound or a precursor thereof.

Any suitable quaternary ammonium compound may be included in component (i).

Some suitable quaternary ammonium compounds have the structure (I):

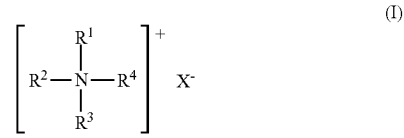

wherein each of $R^1$, $R^2$, $R^3$ and $R^4$ is an optionally substituted alkyl, alkenyl, alkylaryl or aryl group and $X^-$ is a suitable anion. Preferably each of $R^1$, $R^2$, $R^3$ and $R^4$ is an optionally substituted alkyl or alkylaryl group, more preferably an unsubstituted alkyl or alkylaryl group.

Any suitable anion X⁻ may be used. X⁻ may be selected from halide, acetate, nitrite, a lower alkyl sulfate, carbonate or alkyl carboxylate. Preferably X⁻ is chloride or bromide.

Each of $R^1$, $R^2$, $R^3$ and $R^4$ may be an unsubstituted alkyl group having from 1 to 30 carbon atoms or an alkylaryl group, for example a benzyl group.

Preferably at least one of $R^1$, $R^2$, $R^3$ and $R^4$ is an unsubstituted alkyl group having at least 6 carbon atoms, preferably at least 8 carbon atoms.

In one preferred embodiment $R^1$ is an alkyl group having from 6 to 30 carbon atoms, preferably from 8 to 24 carbon atoms, suitably from 8 to 20 carbon atoms, for example from 10 to 18 carbon atoms and most preferably from 12 to 16 carbon atoms; each of $R^2$ and $R^3$ is an alkyl group having from 1 to 4 carbon atoms, preferably methyl and $R^4$ is an alkyl group having from 1 to 4 carbon atoms, preferably methyl or an alkylaryl group, preferably benzyl. The skilled person will appreciate that such compounds may often be present as a mixture of homologues.

Suitable quaternary ammonium compounds of this type include benzyldialkyl methyl ammonium chloride and dialkyl dimethyl ammonium chloride in which the alkyl groups have 10 to 24 carbon atoms.

Some preferred quaternary ammonium compounds of this type include didecyl dimethyl ammonium chloride and dimethyl benzyl alkyl ammonium chloride in which the alkyl group contains a mixture of $C_8$ to $C_{16}$ alkyl chains.

Some suitable quaternary ammonium compounds include a substituted pyridinium compound for example an alkyl or alkenyl substituted pyridinium compound. Examples include pyridinium compounds having an alkyl or alkenyl substituent of 8 to 30, preferably 10 to 20 carbon atoms. Preferred counterions are halides. One suitable compound of this type is cetylpyridinium chloride.

Some suitable precursor compounds of this type are compounds including a guanidine moiety. The composition may comprise a compound which does not contain a permanent cation but which is protonated in solution at the pH at which the composition is used. These may be referred to as precursors to quaternary ammonium compounds. Preferred are non-polymeric guanidine compounds. Examples of such compounds include chlorhexidine salts, Chlorhexidine gluconate is especially preferred.

In some especially preferred embodiments of the method of the first aspect of the present invention the composition comprising the cell or capsid is contacted with a composition comprising a quaternary ammonium compound including a silicon-containing functional group. By silicon-containing group we mean to refer to any group including a silicon atom. Preferred silicon-containing functional groups are those which include a silicon atom covalently bonded via four single bonds to four organic moieties. The silicon atom may be directly bonded to oxygen and/or carbon atoms.

Preferably the method of the first aspect of the present invention component (i) comprises a compound of general formula (II):

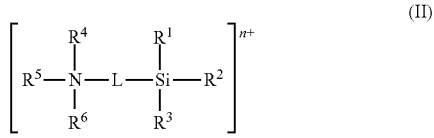

(II)

or a derivative salt thereof wherein L is a linking group; each of $R^1$, $R^2$, $R^3$, $R^5$ and $R^6$ is independently selected from H or an optionally substituted alkyl, alkenyl, aryl or alkoxy group; and n is 0 or 1.

It will be appreciated that in embodiments in which n is 1, the species shown in formula (I) is a cationic species.

In such embodiments the species of formula (I) will be present as an adduct or salt including a suitable counterion. However for ease of reference, in this document we may make general reference to compounds of formula (I) and any such reference includes where appropriate any counterion which must be present.

Any suitable counterion may be used. Monovalent counterions are preferred. Suitable counterions include halides and oxyhalo ions for example chloride, bromide, bromite, chlorite, hypochlorite, chlorate, bromate and iodate. In a most preferred embodiment the counterion is a chloride ion.

In this specification any optionally substituted alkyl, alkenyl, aryl or alkoxy group may be optionally substituted with one or more substituents selected from halo, hydroxy, nitro, mercapto, amino, alkyl, alkoxy, aryl, sulfo and sulfoxy.

Preferred substituents which may be present in the alkyl, alkenyl, aryl or alkoxy groups defined herein are halogens, in particular fluorine. In particular each of $R^1$, $R^2$, $R^3$, $R^4$, $R^5$ or $R^6$ may comprise fluoroalkyl or fluoroalkoxy groups which may comprise one or more fluorine atoms.

Each of $R^1$, $R^2$ and $R^3$ is independently selected from an optionally substituted alkyl, alkenyl, aryl or alkoxy group. Preferably at least one of $R^1$, $R^2$ and $R^3$ is an optionally substituted alkoxy group. More preferably each of $R^1$, $R^2$ and $R^3$ is an optionally substituted alkoxy group, most preferably each is an unsubstituted alkoxy group. The alkyl group of the alkoxy group may be straight chained or branched. Preferably each of $R^1$, $R^2$ and $R^3$ is an alkoxy group having from 1 to 20 carbon atoms, preferably from 1 to 16 carbon atoms, more preferably from 1 to 12 carbon atoms, preferably from 1 to 8 carbon atoms, suitably from 1 to 6 carbon atoms, more preferably from 1 to 4 carbon atoms.

In preferred embodiments each of $R^1$, $R^2$ and $R^3$ is independently selected from methoxy, ethoxy, propoxy, butoxy and isomers thereof. Most preferably each of $R^1$, $R^2$ and $R^3$ is selected from methoxy, ethoxy and isopropoxy. Preferably each of $R^1$, $R^2$ and $R^3$ is selected from methoxy and ethoxy. Most preferably each of $R^1$, $R^2$ and $R^3$ is methoxy. Preferably each of $R^1$, $R^2$ and $R^3$ is the same.

$R^4$ and $R^6$ is preferably an alkyl group having from 1 to 8 carbon atoms, most preferably 1 to 6 carbon atoms, more preferably 1 to 4 carbon atoms. $R^4$ and $R^6$ may suitably be selected from methyl, ethyl, propyl, butyl and isomers thereof. Preferably $R^4$ and $R^6$ is methyl or ethyl. Most preferably $R^4$ and $R^6$ is methyl.

Preferably $R^5$ is an alkyl group having from 8 to 30 carbon atoms, for example from 10 to 26 carbon atoms, suitably from 12 to 24 carbon atoms, preferably from 14 to 22 carbon atoms, suitably from 16 to 20 carbon atoms, for example 17 to 19 carbon atoms, suitably 18 carbon atoms.

L is a linking group. It may suitably be a bond or an optionally substituted alkylene, alkenylene or arylene group. Preferably L is an optionally substituted alkenylene group. It may be substituted along the chain or within the chain. For example L may be an ether linking moiety, i.e. a group of formula $O(CH_2)_n$ in which n is 1 to 12, preferably 1 to 6.

Preferably L is an unsubstituted alkylene group, more preferably an alkylene group having 1 to 12 carbon atoms, preferably 1 to 10 carbon atoms, suitably 1 to 8 carbon atoms, for example 2 to 8 carbon atoms, more preferably 2 to 6 carbon atoms, suitably 2 to 5 carbon atoms for example 2 to 4 carbon atoms. In especially preferred embodiments L is a propylene group.

In especially preferred embodiments of the compound of formula (I), $R^1$, $R^2$ and $R^3$ are each $C_1$ to $C_4$ alkoxy, L is a $C_2$ to $C_5$ alkylene group, $R^4$ and $R^6$ are each $C_1$ to $C_4$ alkyl groups and $R^5$ is a $C_{12}$ to $C_{24}$ alkyl group.

Most preferably the compound of formula (I) is the compound shown in formula (IV). This compound is commercially available as a solution in methanol.

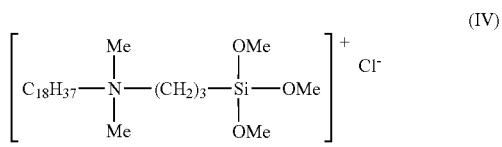

The skilled person will appreciate that commercial sources of such compounds may include some residual starting material and other minor impurities.

Preferably component (i) is selected from quaternary ammonium salts of formula (I), pyridinium salts, guanidine salts and compounds of formula (II).

More preferably component (i) comprises a compound of formula (II).

Most preferably component (i) comprises a compound of formula (IV).

In preferred embodiments the composition contacted with the sample in step (a) of the method of the present invention further comprises (ii) a non-ionic surfactant.

Component (ii) may be selected from any suitable non-ionic surfactant. Suitable non-ionic surfactants will be known to the person skilled in the art and include alcohol ethoxylates, fatty acid esters and alkyl polyglycosides.

Non-ionic surfactants may have a hydrophilic portion, suitably an alkoxylate moiety or a sugar moiety. Suitable non-ionic surfactants include alcohol ethoxylates and fatty alcohol polyglucosides. Suitably the hydrophilic-lipophilic balance (HLB) value of a non-ionic surfactant used in the present invention is at least 7, and preferably at least 10. Especially suitable non-ionic surfactants may have an HLB value falling in the range 10-16, preferably 10-14. For the purposes of these definitions HLB value is determined by the classical method of Griffin (Griffin WC: "Calculation of HLB Values of Non-Ionic Surfactants," Journal of the Society of Cosmetic Chemists 5 (1954): 249).

Preferred non-ionic surfactants for use herein include hydrocarbyl saccharide compounds. By hydrocarbyl-saccharide compound we mean to refer to a compound including a hydrocarbyl group and a saccharide moiety.

The hydrocarbyl group may be bound to the saccharide moiety via a carbon-carbon bond or via a carbon-oxygen bond. Preferably it is bound to the saccharide moiety via a carbon-oxygen bond, for example via an ester linkage or an ether linkage. Most preferably it is bound to the oligosaccharide moiety via an ether linkage. Thus in preferred embodiments the non-ionic surfactant is a hydrocarbyl ether of a saccharide moiety.

The hydrocarbyl-saccharide compound may include one or more hydrocarbyl groups. Preferably it comprises one hydrocarbyl group. The hydrocarbyl group may be an optionally substituted alkyl, alkenyl or alkynylene group. Most preferably it is an optionally substituted alkyl group. Suitable substituents include halo, hydroxy, nitro, mercapto, amino, alkyl, alkoxy, aryl, sulfo and sulfoxy. Any substitution may be within the chain or along it, for example the chain may include an ether linkage.

Preferably the hydrocarbyl group is an unsubstituted alkyl group. It may be straight chained or may be branched. Most preferably it is straight chained. Especially preferred hydrocarbyl groups are alkyl groups having from 1 to 30 carbon atoms, preferably 2 to 24 carbon atoms, more preferably from 4 to 20 carbon atoms, suitably from 4 to 16 carbon atoms, preferably from 6 to 14 carbon atoms, for example from 6 to 12 carbon atoms and most preferably from 8 to 10 carbon atoms. Preferred are straight chained alkyl groups having from 6 to 12 carbon atoms.

The saccharide moiety of the hydrocarbyl oligosaccharide species may include from 1 to 10 monosaccharide species. Thus it may be a monosaccharide unit, a disaccharide unit or an oligosaccharide unit. Preferably the saccharide moiety comprises from 2 to 8, suitably from 2 to 6, preferably from 2 to 5, for example 3 or 4 monosaccharide units. Any suitable monosaccharide unit may be included. Preferred saccharides include allose, altrose, glucose, mannose, gulose, idose, galactose and talose.

Mixtures of two or more monosaccharides may be present in the saccharide moiety. Preferably the saccharide moiety comprises glucose. More preferably all of the monosaccharide units present in the saccharide moiety are glucose.

In a preferred embodiment the non-ionic surfactant is an alkyl polyglucoside (APG), preferably a monoalkyl-polyglucoside. Suitably the non-ionic surfactant is a compound of general formula (III):

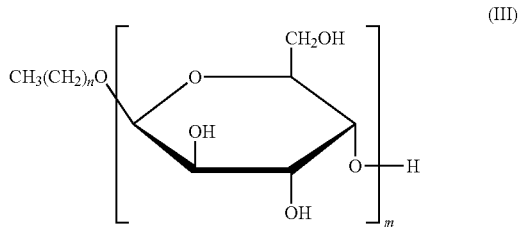

wherein n is from 5 to 12, preferably from 6 to 10, more preferably from 7 to 9 and m is from 1 to 6, preferably from 2 to 5, more preferably 3 or 4.

The composition contacted with the sample in step (a) of the method of the first aspect may be provided in any suitable form. It may consist essentially of component (i) or component (i) and a solvent. It may consist essentially of components (i) and (ii) or it may comprise one or more further components. Suitably the composition includes one or more solvents. Preferred solvents are water and water miscible solvents. In embodiments in which the quaternary ammonium compound is obtained commercially as a solution in methanol, much of the methanol is suitably removed prior to use of the compound in the method of the present invention.

Preferably the composition is aqueous. In especially preferred embodiments water comprises at least 90 wt %, more preferably at least 95 wt % or at least 99 wt % of all solvents present in the composition. In one preferred embodiment the composition is freeze dried. In such embodiments an aqueous mixture may be provided upon contact with an aqueous composition comprising the cells or capsids. Freeze-dried compositions may be advantageous for storage and distribution.

In some embodiments the composition used in step (a) may be immobilised on a solid support, for example on a resin bead or on a planar substrate.

The composition used in step (a) of the method of the present invention may include a mixture of two or more quaternary ammonium compounds and/or a mixture of two or more non-ionic surfactants.

The composition contacted with the sample in step (a) of the method of the present invention preferably comprises at least 0.0001 wt % of a quaternary ammonium compound, preferably at least 0.0005 wt %, more preferably at least 0.001 wt %, and more preferably at least 0.002 wt %.

The quaternary ammonium compound preferably comprises up to 10 wt % of the composition contacted with the sample in step (a), suitably up to 5 wt %, preferably up to 1 wt %, preferably up to 0.1 wt %, more preferably up to 0.01 wt %, and more preferably up to 0.005 wt %.

In embodiments in which more than one quaternary ammonium compound is present, the above amounts refer to the total of all such compounds.

The non-ionic surfactant is suitably present in the composition contacted with the sample in step (a) in an amount of at least 0.0001 wt %, preferably at least 0.0005 wt %, more preferably at least 0.001 wt %, and more preferably at least 0.002 wt %.

The non-ionic surfactant may be present in the composition contacted with the sample in step (a) in an amount of up to 10 wt % of the composition, suitably up to 5 wt %, preferably up to 1 wt %, preferably up to 0.1 wt %, more preferably up to 0.01 wt %, and more preferably up to 0.005 wt %.

In embodiments in which the composition comprises two or more non-ionic surfactants the above amounts refer to the total of all such compounds.

The weight ratio of the quaternary ammonium compound functional component to the non-ionic surfactant is preferably from 1:10 to 10:1, preferably from 1:5 to 5:1, preferably from 1:3 to 3:1, suitably from 1:2.5 to 2.5:1.

The composition contacted with the sample in step (a) preferably has a pH of from 6 to 8.

The composition contacted with the sample preferably comprises (i) a quaternary ammonium compound and (ii) a non-ionic surfactant. In some embodiments the composition may consist essentially of these components.

In some embodiments the composition further includes a solvent, preferably water.

Other components may also be present, for example magnesium chloride and tris buffers. However this is not preferred.

Suitably components (i) and (ii), which may each comprise a mixture of components, together make up at least 50 wt % of all ingredients other than solvent present in the composition used in step (a), preferably at least 70 wt %, more preferably at least 90 wt %, preferably at least 95 wt %, for example at least 99 wt %.

Preferably the composition used in step (a) of the method of the present invention comprises less than 0.01 mmol of magnesium ions, preferably less than 0.001 mmol.

In step (a) of the method of the first aspect of the present invention the sample is contacted with a composition comprising (i) a quaternary ammonium compound and optionally (ii) a non-ionic surfactant. Suitably the ratio of the sample composition (e.g. blood) to the composition used in step (a) is from 10:1 to 1:1000, preferably from 5:1 to 1:100, suitably from 1:1 to 1:20 for example from 1:3 to 1:10, by volume.

Suitably the composition is agitated to ensure mixing.

Step (b) involves contacting the sample with a probe which is capable of interacting with the target nucleic acid sequence.

Steps (a) and (b) may be carried out in either order. In some embodiments step (a) and step (b) may be carried out simultaneously. Thus the present invention may involve contacting a sample with a composition comprising:
 (i) a quaternary ammonium compound or a precursor thereof; optionally
 (ii) a non-ionic surfactant and
 (iii) a probe which is capable of interacting with a target nucleic acid sequence.

In some embodiments step (b) may be carried out before step (a). In preferred embodiments step (b) is carried out after step (a).

It has been surprisingly found that the mixture obtained in step (a) of the present invention can be used directly in step (b) without the need for complex purification steps.

It is highly advantageous that the method of the present invention provides a simple process in which DNA and/or RNA suitable for direct detection using molecular techniques can be released directly from a sample, for example whole blood, saliva and other liquid biopsies. When the target is an RNA component a reverse transcription step is necessary. Methods of carrying out such steps are known to the person skilled in the art.

It is a further advantage of the present invention that nucleic acid is provided in step (a) in a stabilised form. This means that after step (a) the sample may be stored and/or transported.

In some embodiments there are no washing or other purification steps between step (a) and (b).

In some embodiments there may be a step between step (a) and step (b) of contacting the sample with a composition comprising a proteinaceous washing agent.

Thus in the same preferred embodiments the method of the present invention involves a step (a2) between step (a) and step (b) of contacting the composition obtained in step (a) with a proteinaceous washing agent.

Preferred proteinaceous washing agents are anionic proteins.

Suitable proteinaceous washing agents include tryptone, gelatin, casein and bovine serum albumin (BSA). Preferred proteinaceous washing agents include bovine serum albumin and casein. An especially preferred washing agent is BSA. Acetylated bovine serum albumin (BSA) is particularly preferred.

Suitably the proteinaceous washing agent is present in the composition used in step (b) in an amount from 0.01 to 50 wt %, preferably 0.1 to 10 wt %, suitably from 0.1 to 5 wt %, for example about 1 wt %.

Suitably the composition comprising a proteinaceous washing agent invention is an aqueous composition. Suitably water comprises at least 90 wt % of all solvents present in the composition, preferably at least 95 wt % for example at least 99 wt % of all solvents present in the composition.

In one embodiment the composition comprising the proteinaceous washing agent may be freeze dried. In such an embodiment an aqueous mixture may be provided upon contact with the aqueous composition obtained in step (a).

Suitably the composition obtained in step (a) is mixed with a composition comprising the proteinaceous washing agent in a ratio of from 10:1 to 1:100, preferably from 5:1 to 1:50, suitably from 1:1 to 1:10.

In one embodiment the composition may be freeze dried. In such an embodiment an aqueous mixture may be provided upon contact with the aqueous composition obtained in step (a).

Suitably the resultant mixture is briefly agitated at room temperature. It may be left for a period of 1 second to 24 hours, suitably 5 seconds to 1 hour, preferably 5 seconds to 30 minutes, preferably 10 seconds to 10 minutes, suitably from 30 seconds to 5 minutes, for example about 1 minute.

Without being bound by theory it is believed that cell lysis occurs during step (a) of the method of the present invention. Thus genetic material is suitably released from the cell. It is believed however that unlike many methods of the prior art the genetic material doe not degrade but is stabilised by the composition contacted with the sample in step (a). This stabilisation is highly advantageous.

Depending on the nature of the sample, the target nucleic acid sequence and the nature of the probe, the composition obtained in step (a) may be used directly in step (b) or it may first be contacted with a composition comprising a proteinaceous washing agent.

Suitable probes for use in step (b) include hybridisation probes and dyes.

Suitable hybridisation probes include single stranded DNA probes, double stranded DNA probes and RNA probes such as cRNA probes or riboprobes. The hybridisation probes may be tagged with radioactive, fluorescent or chemiluminescent molecules, suitably fluorescent molecules.

Suitable dyes include fluorescent and chemiluminescent dyes, suitably fluorescent dyes. Examples of suitable dyes will be known to the person skilled in the art and include those sold under the trade marks Syber Green, Syber Gold and Syber Safe.

Suitably the probe(s) interact with target nucleic acid sequence when present. By this we mean that when the probe comes into contact with the target nucleic acid sequence it interacts or binds in some way. This results in a change in the probe, typically a change in conformation. This change causes the probe to release a signal and this signal may be detected. For example the probe may intercalate with the nucleic acid or the probe may bind directly to the nucleic acid.

In step (b) of the method of the present invention a probe is contacted with the sample. If the target nucleic acid sequence is present, the probe will interact with the target nucleic acid and will provide a signal.

If the target nucleic acid is not present there will be no interaction and no signal.

Step (c) of the method of the present invention involves observing and/or measuring a property of the sample.

In some embodiments the probe may fluoresce on binding and thus observing the sample will provide a qualitative determination of whether or not the target nucleic acid sequence is present.

Step (c) may involve a qualitative or quantitative analysis. For example it may involve observing fluorescence or measuring the intensity of the light produced.

Quantitative measurement can be used to estimate the concentration of the target nucleic acid sequence in the sample.

In some embodiments the present invention may involve amplifying the target nucleic acid. However this is not preferred.

Methods for detecting the presence or absence of target nucleic acid suitable for use in steps (b) and (c) include DNA and/or RNA hybridisation methods, microarrays and melt analysis, such as high resolution melt (HRM) analysis or microscale thermophoresis.

In some embodiments steps (b) and (c) may involve contacting the sample with a hybridisation probe and subsequently detecting the presence or absence of target nucleic acids using DNA and/or RNA hybridisation methods.

In some embodiments steps (b) and (c) may involve contacting the sample with a fluorescent hybridisation probe and subsequently detecting the presence or absence of the target nucleic acid sequence using a fluorescent DNA and/or RNA hybridisation method. Suitably the fluorescent DNA and/or RNA hybridisation method involves the use of one or more fluorescent hybridisation probe(s).

The use of the fluorescent hybridisation probe allows detection of target nucleic acid. The fluorescent hybridisation probe(s) act to bind to nucleic acid when they recognise a specific nucleic acid sequence they are complementary to. Upon binding to the nucleic acid sequence the probe fluoresces. This fluorescence is then visualised using techniques well known to a person skilled in the art. The fluorescence may be visualised with the aid of graphical representation.

In some embodiments the DNA and/or RNA hybridisation method may be a microarray (chip-on-chip).

In some embodiments steps (b) and (c) may involve contacting the sample with a fluorescent dye and subsequently detecting the presence or absence of target nucleic acid using melt analysis, suitably high resolution melt (HRM) analysis.

The use of high resolution melt analysis allows detection of target nucleic acid. The fluorescent dye(s) act to come into contact, such as to intercalate, with the nucleic acid and, upon binding, the fluorescent dyes are caused to fluoresce more brightly than when they are unbound. The samples are then heated and the level of fluorescence decreases as the sample heats up. The level of fluorescence may be visualised with the aid of graphical representation, such as in the form of a melt curve. The profile of a melt curve for a target nucleic acid sequence will typically be different for 'wild type' DNA and/or RNA and those having a mutation therein.

In some embodiments melt analysis may involve the use of multiple probes which have different characteristic melt curves in a high resolution melt analysis method. The use of multiple probes may allow the detection of multiple targets in a single sample.

In some embodiments the method of the present invention may be used in the detection or diagnosis of a disease. The method may be used to detect or diagnose, among others, genetic diseases, cancers, autoimmune diseases and pathogenic diseases. Genetic markers indicative of disease are identified in steps (b) and (c). One particular advantage of the present invention is that because samples do not need to be purified before or after step (a) there is significant reduction in the time taken to reach diagnosis. There are also significant cost savings as purification steps are avoided.

Another particular advantage of the present invention is that because the composition obtained in step (a) is stable and the nucleic acid does not degrade, the sample can be stored and/or transported between steps (a) and (b).

However for qualitative analysis a very simple method that can be used in the field may be provided whereby a sample is contacted with a composition according to step (a) and then contacted with a composition comprising a fluorescent probe. The presence or absence of fluorescence provides an immediate visual indication of whether the target nucleic acid is present and hence whether the individual who provided the sample infected with a particular disease.

An advantage of the present invention is that because it does not necessarily involve the use of PCR or other complex techniques, expensive specialist equipment is not needed.

In some embodiments the invention may involve the use of DNA/RNA hybridisation methods. However in some embodiments the invention may simply involve contracting the sample with a number of aqueous compositions, one of which contains a fluorescent probe and observing the presence or absence of fluorescence. In such embodiments the invention may provide a simple, point of care device which allows a quick, simple, cheap, qualitative diagnosis to be made.

A further advantage of the invention is that the stabilisation provided in step (a) allows RNA to be detected. As RNA is more prevalent than DNA this can provide a lower limit of detection. Furthermore RNA often provides more accurate information regarding the current status of a cell.

In embodiments in which the target is an RNA component, the method of the invention suitably involves a reverse transcription step between step (a) and step (b). However because the sample obtained in step (a) is stable, RNA does not degrade enabling the resulting agent to be readily detected using a probe in step (b).

In some embodiments the method of the present invention may be used to detect or diagnose infection with a pathogenic disease. Suitably the method of the present invention may be used to detect or diagnose infection with a pathogenic disease is which a target nucleic acid sequence characteristic of the pathogenic microorganism can be identified.

Suitable pathogenic organisms include pathogenic bacteria of the genera *Bacteroides, Bartonella, Bordetella, Borrelia, Brucella, Campylobacter, Chlamydia, Escherichia, Francisella, Haemophilus, Helicobacter, Klebsiella, Legionella, Leptospira, Moraxella, Neisseria, Pasteurella, Proteus, Pseudomonas, Salmonella, Shigella, Spirillum, Streptobacillus, Treponema, Vibro, Yersinia, Actinomyces, Bacillus, Clostridium, Corynebacterium, Listeria, Nocardia, Peptostreptococcus, Propionibacterium, Staphylococcus, Streptococcus* and *Streptomyces*, pathogenic protozoa of the genera *Acanthamoeba, Ancylostoma, Ascaradia, Babesia, Balamuthia, Balantidium, Brugia, Clonorchis, Cryptosporidium, Dicrocoelium, Dicytocaulus, Dientamoeba, Diphylobothrium, Dirofilaria, Echinococcus, Echinostoma, Entamoeba, Enterobius, Fasciola, Fascioloides, Giardia, Hymenolepsis, Isospora, Leishmania, Mesocestoides, Moniezia, Necator, Naegleria, Onchocerca, Opisthorchis, Paragonimus, Plasmodium, Rhabditida, Schistosoma, Spirurida, Strongyloides, Taenia, Trichomonas, Trichuris, Toxocara, Trypanosoma, Uncinaria* and *Wuchereria*.

In some embodiments the method of the present invention may be used to detect or diagnose cancers.

Suitable cancers include cancers derived from brain cells, epithelial cells (carcinoma), connective tissue (sarcoma), hematopoietic cells (lymphoma and leukemia), pluripotent cells (germ cell tumour), and embryonic tissue (blastoma). Suitable cancers include, among others, breast cancer, brain cancer, liver cancer, stomach cancer, skin cancer, prostate cancer, cervical cancer, lung cancer.

In some embodiments the method of the present invention may be used to detect or diagnose autoimmune diseases. Autoimmune diseases commonly affect organ and tissue types such as blood vessels, connective tissues, endocrine glands, joints, muscles, red blood cells, and the skin.

Suitable example of autoimmune diseases include, among others, Addison's disease, celiac disease, dermatomyositis, Graves' disease, Guillan-Barre disease, inflammatory bowel disease, multiple sclerosis, pernicious anaemia, psoriasis, rheumatoid arthritis, systemic lupus erythematosus and type I diabetes.

The method of the present invention may have particular utility in the field of personalised medicine where specific mutations in, for example, a cancer can be used to prescribe particular drugs.

The method of the present invention may have particular utility in the field of companion diagnostics.

EXAMPLE 1

Composition A was prepared comprising, in an aqueous solution:
0.003 wt % of a quaternary ammonium compound having the formula:

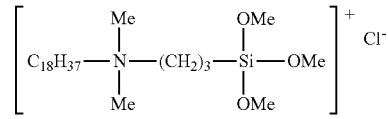

0.003 wt % of an alkyl polyglucoside alkyl polyglucoside comprising a mixture of isomers of formula:

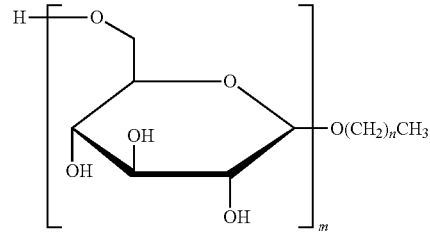

where n=7 or 9 and m=1 to 5; and
Composition B was prepared comprising water and 1 wt % acetylated bovine serum albumin (BSA).

EXAMPLE 2

An HCV melting probe was used to test direct melting over the retro-transcribed cDNAs from a real clinical sample. A defrosted serum sample from a positively diagnosed hepatitis C patient sample was treated alongside a negative serum sample for control.

30 µL of the serum sample were mixed with 3 µL of composition A and 167 µL of water (molecular biology grade). The mix was vortexed and incubated at room temperature 1 minute. 2.5 µL of the product was mixed with 10 µL of composition B.

Figure 1:
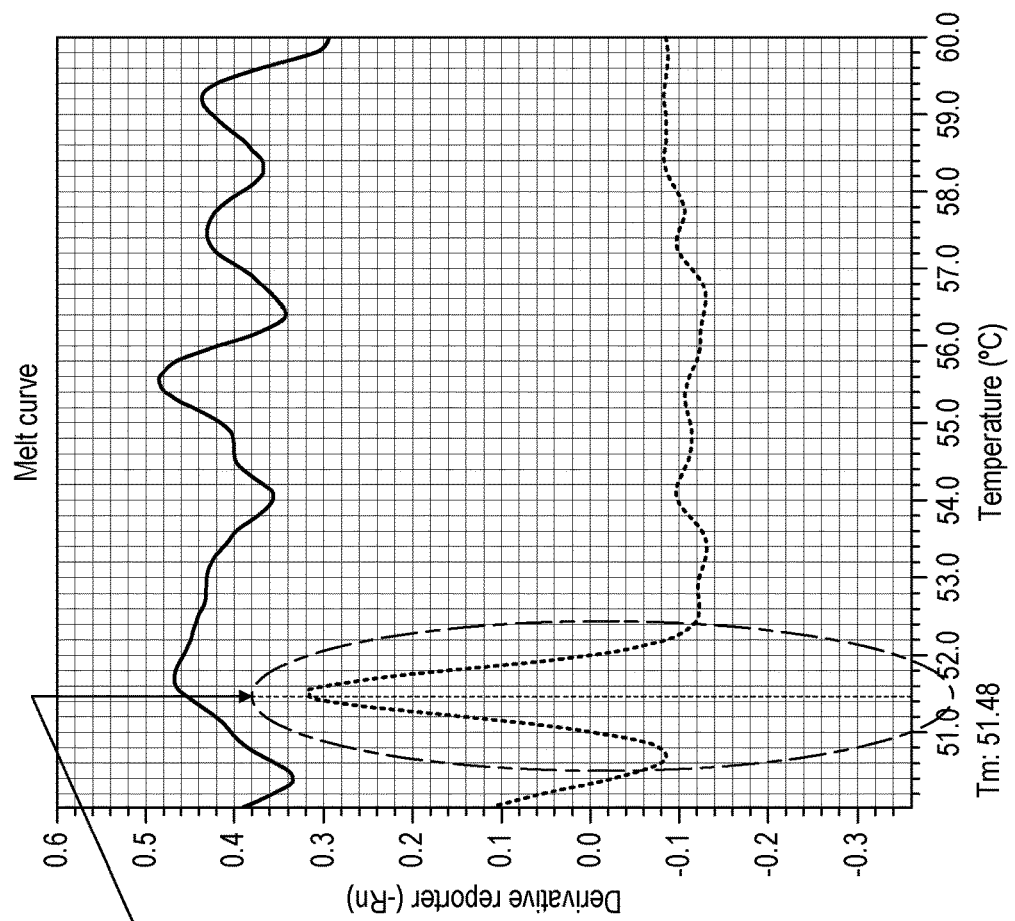
FIG. 1 shows a melt curve of Example 2, described below.
Figure 1:
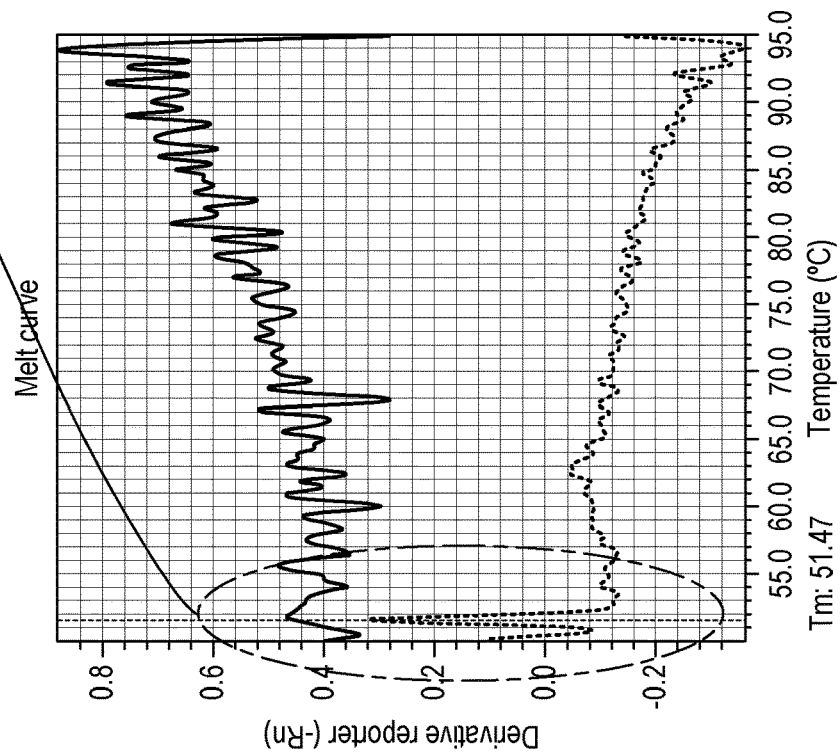

A standard RT was performed, followed by a Melting Stage as per the program below:

48° C. 30 min ⟶ RT profile
95° C. 5 min
50° C. 60 sec ⎫
95° C. 15 sec ⎭ Melting profile The resulting melt curve is shown in FIG. 1.

EXAMPLE 3

One defrosted blood sample formerly identified as positive for *Plasmodium* spp. and one defrosted blood sample formerly identified as negative for *Plasmodium* spp. were used.

30 μL of the blood samples were mixed with 3 μL of composition A and 167 μL of water (molecular biology grade). The mix was vortexed and incubated at room temperature 1 minute. 2.5 μL of the product was mixed with 10 μL of composition B.

A single step of RT for *Plasmodium* spp in StepOnePlus System (Applied Biosystems) was performed under the following thermal profile, which is exclusive for retro-transcription and doesn't include PCR. A subsequent melting between 50° C. and 90° C. was set for direct detection[1].

48° C. 30 min ⟶ RT profile
95° C. 5 min
50° C. 60 sec ⎫ Melting profile
95° C. 15 sec ⎭ (0.3 deg dwell)

Figure 2:
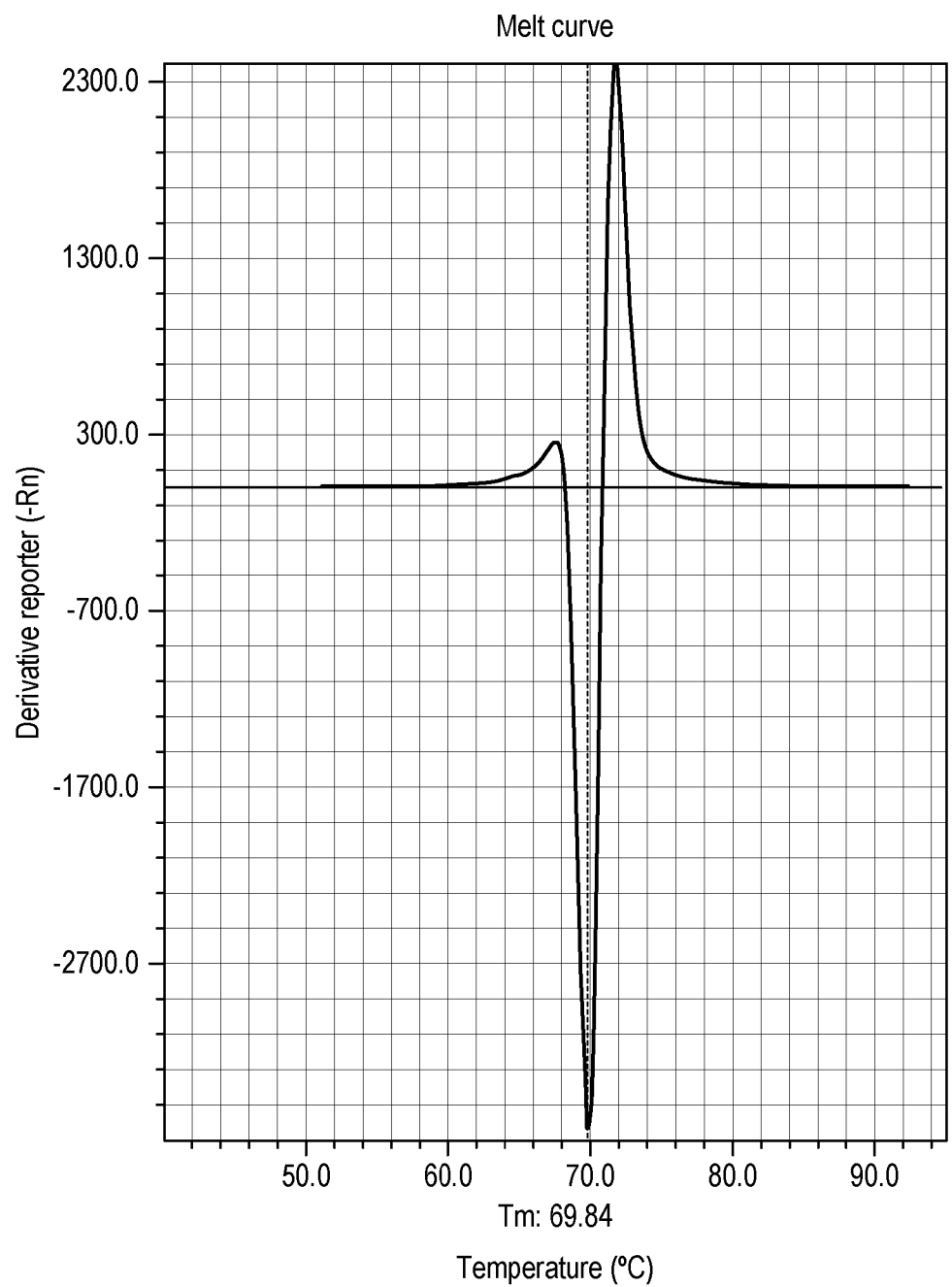
FIG. 2 shows a melt curve of Example 3, described below.
The invention will now be further defined with reference to the following non-limiting examples.

The melt curve is shown in FIG. 2.

The invention claimed is:

1. A method of determining of the presence or absence of a target nucleic acid component in a sample, without amplification of said target nucleic acid component, the method comprising steps of:
   (a) contacting the sample with a composition comprising:
      (i) a quaternary ammonium compound including a silicon-containing group;
   (b) contacting the composition obtained in step (a) with a proteinaceous washing agent;
   (c) contacting the sample with a probe which is capable of interacting with the nucleic acid sequence; and
   (d) observing and/or measuring a property of the sample.

2. A method according to claim 1 wherein the sample is a sample of bodily fluid or tissue obtained from a human.

3. A method according to claim 1, wherein the composition contacted with the sample in step (a) of the method of the present invention further comprises (ii) a non-ionic surfactant.

4. A method according to claim 3 wherein the non-ionic surfactant is an alkyl polyglucoside.

5. A method according to claim 1, wherein step (c) is carried out after step (a).

6. A method according to claim 1, wherein step (d) involves observing the presence or absence of fluorescence.

7. A method according to claim 1, wherein steps (c) and (d) involve contacting the sample with a fluorescent dye and subsequently detecting the presence or absence of target nucleic acid using melt analysis.

* * * * *